(12) United States Patent
Hearn

(10) Patent No.: US 9,763,474 B2
(45) Date of Patent: Sep. 19, 2017

(54) SIMULATED CIGARETTE

(75) Inventor: Alex Hearn, London (GB)

(73) Assignee: Kind Consumer Limited, London (GB)

( * ) Notice: Subject to any disclaimer, the term of this patent is extended or adjusted under 35 U.S.C. 154(b) by 1125 days.

(21) Appl. No.: 13/636,563

(22) PCT Filed: Mar. 23, 2011

(86) PCT No.: PCT/GB2011/000416
§ 371 (c)(1),
(2), (4) Date: Nov. 21, 2012

(87) PCT Pub. No.: WO2011/117580
PCT Pub. Date: Sep. 29, 2011

(65) Prior Publication Data
US 2013/0061861 A1 Mar. 14, 2013

(30) Foreign Application Priority Data

Mar. 23, 2010 (GB) .................................. 1004861.9

(51) Int. Cl.
*A24F 47/00* (2006.01)
(52) U.S. Cl.
CPC .......... *A24F 47/006* (2013.01); *A24F 47/002* (2013.01)
(58) Field of Classification Search
CPC .... A24F 47/002; A24F 47/004; A24F 47/006; A24F 47/008; A24F 47/00; A61M 15/06
See application file for complete search history.

(56) References Cited

U.S. PATENT DOCUMENTS

| 3,185,162 | A | * | 5/1965 | Fiore ..................... A24B 15/12 131/370 |
| 3,631,856 | A | | 1/1972 | Taylor |
| 4,284,089 | A | * | 8/1981 | Ray ....................... A24F 47/002 128/202.21 |
| 4,765,347 | A | * | 8/1988 | Sensabaugh, Jr. .... A24F 47/002 131/173 |
| 4,945,931 | A | | 8/1990 | Gori |

(Continued)

FOREIGN PATENT DOCUMENTS

| EP | 0149997 A2 | 7/1985 |
| EP | 0758695 B1 | 2/1997 |

(Continued)

OTHER PUBLICATIONS

Smook, Handbook for Pulp and Paper Technologists, 1992, Angus Wilde Publications, 2nd edition, chapter 15.*

(Continued)

*Primary Examiner* — Anthony Calandra
(74) *Attorney, Agent, or Firm* — Patterson & Sheridan, L.L.P.

(57) ABSTRACT

A simulated cigarette which has a reservoir of an inhalable composition and an outlet valve to control the outlet flow. The outlet end is provided with a deformable material to provide a more realistic feel and optionally to allow the user to vary the flow characteristics in the manner of a real cigarette. The outlet end can also be provided with a chemical heater. The simulated cigarette is wrapped in a paper or paper-like wrap to provide a more realistic feel.

4 Claims, 4 Drawing Sheets

(56) References Cited

U.S. PATENT DOCUMENTS

Figure 1:
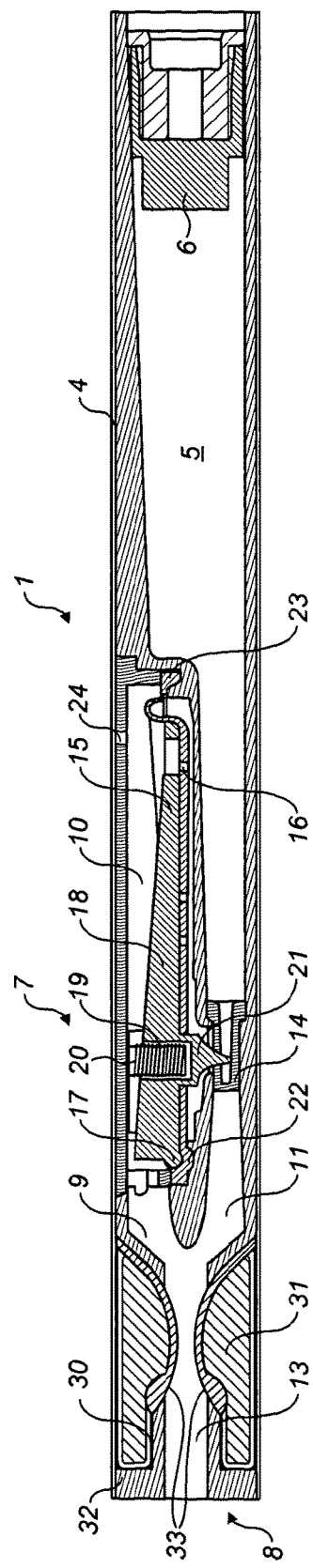

| | | | | |
|---|---|---|---|---|
| 5,294,299 A | * | 3/1994 | Zeuner | D21H 21/52 |
| | | | | 162/145 |
| 2009/0235939 A1 | * | 9/2009 | Gonsalves | A24D 1/14 |
| | | | | 131/191 |
| 2010/0059070 A1 | | 3/2010 | Potter et al. | |
| 2014/0137880 A1 | * | 5/2014 | Zitturi | A24D 1/02 |
| | | | | 131/337 |

FOREIGN PATENT DOCUMENTS

| | | | | |
|---|---|---|---|---|
| EP | 1656842 A1 | | 5/2006 | |
| FR | 2665639 A1 | | 2/1992 | |
| GB | WO 2009001082 A1 | * | 12/2008 | ........... A24F 47/002 |
| JP | H0383571 A | | 4/1991 | |
| JP | H04262712 A | | 9/1992 | |
| JP | 3018684 U | | 11/1995 | |
| WO | 2009022232 A2 | | 2/2009 | |
| WO | 2009156181 A3 | | 12/2009 | |
| WO | 2013/034039 A1 | | 3/2013 | |

OTHER PUBLICATIONS

International search report and written opinion for application No. PCT/GB2011/000416 dated Oct. 24, 2011.

EPO Examination Report dated Oct. 27, 2015, for EPO Patent Application No. 13182436.9.

English translation of Japanese Office Action dated Jun. 7, 2016, for Japanese Patent Application No. 2015-114967.

* cited by examiner

SIMULATED CIGARETTE

The present invention relates to a simulated cigarette comprising a housing having a generally cigarette-like shape and size; a reservoir of inhalable composition within the housing; an outlet valve controlling the flow from the reservoir; an outlet passage from the outlet valve to an outlet in the housing from which outlet a user inhales the composition. Such a simulated cigarette will subsequently be referred to as "of the kind described".

A simulated cigarette of the kind described is disclosed in our earlier WO 2009/001078 and WO 2009/001082.

These documents disclose a simulated cigarette device which is refillable in combination with a refill pack which has a size and shape of a cigarette pack. The user removes the simulated cigarette from the pack and holds it against an outlet port in the pack to refill it. This is designed to mimic the action of removing a real cigarette from a pack. By replicating the smoking act, the device is more likely to gain acceptance from a consumer.

However, the simulated cigarette device disclosed in these applications and, indeed, similar cigarette devices disclosed in other applications such as U.S. Pat. No. 4,393,884 and DE 4030257 are simply cylindrical plastic tubes.

The present invention aims to provide a simulated cigarette device which more closely resembles the physical feel of a real cigarette.

According to a first aspect of the present invention, a simulated cigarette of the kind described is characterised in that the housing adjacent to the outlet end has a deformable material at its outer periphery.

This deformable material is able to be squeezed or flexed by the index finger and thumb of a smoker. This is an important feature for a smoker and part of the behavioural cycle of the smoking ritual. The first aspect of the present invention therefore provides a tactile sense akin to a conventional cigarette. Also, the deformable material provides a more realistic smoking experience for the user when it comes to inhalation. Users typically purse inhalation devices with their lips or teeth so it is advantageous to make the material against which they press deformable accordingly.

As well as providing increased comfort, the deformable material can also be used to affect the flow characteristics of the inhalable composition. Preferably, the deformable material is configured to be deformable with respect to the outlet passage to change the flow characteristics from the outlet passage. With such a deformable material, the user can disrupt the flow of inhalable material giving rise to vortices that will modify the delivery from the reservoir. This mimics the manner in which smokers modify the delivery of a conventional tobacco cigarette by squeezing the filter to reduce the pore size thereby modifying the flow of the smoke accordingly. This allows the user to modify the flow by narrowing the outlet passage and thereby quickening the velocity of the flow.

In order to further enhance the control being exercised by a user, the outlet valve is preferably a breath-activated valve which is actuated by a flow of air through the housing in an actuation passage parallel to the flow through the outlet passage and wherein the deformable material is positioned so that it is deformable into the housing to a position in which it affects the flow through at least one of the actuation passage and the outlet passage so as to affect the dosage of inhalable composition that a user receives from the cigarette.

If the user constricts the actuation passage, the suction force required to open the valve increases while constricting the outlet passage increases the velocity of the flow. This is an important adaptable behavioural mode for smokers since when they desire a deeper inhalation, normally in a spike of craving, they can modify the suction chamber through this action and modestly increase the velocity of the flow, and therefore the speed of uptake to the lung allowing sophisticated control of the flow characteristics. Additionally if the user exerts a lower than usual suction force and constricts the chamber, the device may function in the opposite manner by creating a limitation on the breath force exerted on the breath-activation system and therefore limiting the valve opening and thus the flow rate by the user. Thus by allowing distortion of the flow path, akin to a tobacco cigarette, a more sophisticated control of the flow characteristics is allowed.

The deformable material may be elastomeric, or may be a flexible skin containing a fluid or gel.

When the deformable material includes liquid or a gel, as a further enhancement of the invention, this may be supersaturated and arranged to come into contact with nucleation sites upon tapping of the cigarette, to form crystals and undergo an exothermic reaction.

This can produce a warming sensation at the tip of the cigarette which a user will find pleasant and again replicates the heating effect in a real cigarette of drawing smoke through the filter.

As the cigarette device is designed to be refilled a number of times, there are preferably a plurality of compartments containing liquid or gel which are separately actuatable to produce an exothermic reaction.

In addition to, or as an alternative to, using the exothermic reaction to provide a warm sensation adjacent to a mouthpiece of a cigarette, the cigarette may be configured to direct the heat produced inwardly, so as to heat the inhalable composition in the outlet passage.

This forms a second aspect of the present invention which may be defined, in the broadest sense, as a simulated cigarette of the kind described further comprising a chemical heater provided adjacent to the outlet passage and arranged to be activated to undergo an exothermic reaction to heat the inhalable composition as it travels along the outlet passage.

The generation of heat in a simulated cigarette is known, for example, in EP 1 618 803 and in WO 2009/155957. However, in these cases, the heat is used to vaporise the composition. In this second aspect of the present invention, the inhalable composition is released from a reservoir and is subsequently heated by a heater.

The inhalable composition is released from the reservoir will generally be cold. It is warmed, to some extent, by the surrounding housing as it travels around the outlet passage and, if present, by dilution of air from the actuation passage. However, if the device is used repeatedly, the mouthpiece itself can become cold to touch. This can be avoided by heating the mouthpiece, which also has a beneficial effect on the temperature of the inhalable composition flowing through the mouthpiece.

Preferably, the outlet valve is at least 4 mm from the outlet. This allows sufficient time for the inhalable composition to mix with ambient air to allow the warming effect referred to above. This allows sufficient time for the inhalable composition to mix with ambient air to allow the warming effect referred to above.

Preferably, the heater is provided by a gel or liquid which is supersaturated and which is arranged to come into contact with nucleation sites upon tapping of the cigarette, to form crystals and undergo an exothermic reaction.

As the cigarette device is designed to be refilled a number of times, there are preferably a plurality of compartments containing liquid or gel which are separately actuatable to produce an exothermic reaction. These components are preferably provided by rupturable microcapsules.

According to a third aspect of the present invention, a simulated cigarette of the kind described is wrapped in a wrap comprising an adhesive layer to stick to the housing, a paper or paper-like layer and a polymer film to cover and protect the paper or paper-like layer.

In the prior art referred to above, all simulated cigarettes of this type have only a plastic housing as they are designed to be durable. US 2004/0003820 discloses a cigarette substitute with a chamber lined with a scratch-releasable-coated paper which is scratched with a wire brush to release a cigarette-like aroma. This document discloses that the vessel is coated or lined with a white, paper-like material for improved realism but there is no indication of the underlying material of the housing, or how this is implemented. JP2010/35663 discloses an inhaler containing a string of capsules. These are crushed by a user's fingers to release their contents for inhalation. The device is covered in a paper-like material as it is required to be deformable to crush the capsules.

The third aspect of the present invention replicates more closely the feel of a real cigarette. Further, it is suited to the arrangement described in WO 2009/001078 which is designed to be refilled only a relatively small number of times such that longevity is less of an issue. The polymer film is able to protect the paper as the time for which it is used, while for less than the prior art above, is still significantly longer than a real cigarette or the devices of US 2004/0003820 and JP 2010/035663.

Preferably, the wrap is hydrophobic so that it does not absorb moisture from the user's mouth, from the ambient environment or from the filling process. The wrap is preferably a wipe-clean paper. It is preferably also fire retardant in case of hazard or mistaken ignition. Preferably, the wrap is provided with a flavour (e.g. menthol) and/or an antibacterial agent.

Such an example of a wrap is a co-extruded biaxially orientated corona treated polyproplyene situated with an acrylic based adhesive. The adhesive is a water-borne acrylic based adhesive comprising acrylic esters copolymerised with acrylic acid.

This is laminated over a supercalendered glassine paper, which gives the image and texture of a paper wrap, where the transparency is around 30-60%, most preferably 45%. A compatible ink, preferably a raw material consisting of an acrylate mixture, which in its finished cured form in a acrylate polymer contains very little residual monomer such to improve the chemical stability of the system. Such a system can also be impregnated with Silver Ion spray coating on top of the glassine paper to limit any microbial activity over continued use, and the end tip can be sprayed with a compatible fire retardant material before the adhesive layer and extruded polypropylene applied.

Additionally a laminate is layered over the system to improve stability and use duration. A higher strength acrylic adhesive is employed to attach the laminate underlay of the glassine paper to the plastic chassis tubing of the inhaler, such that it will remain in fixed position without uncurling or unwrapping over the alotted shelf life. Such a system should incorporate as low a density co-extruded biaxially orientated corona treated polyproplyene as possible without compromising resistance, in order to improve the fixation stability of the wrap.

The system should comply with the guidelines laid down under ISO 10993 when relating to component biocompatibility. As such, plastic coating should comply with a material safety test guidance under the European Pharmacopiea in order to ensure compatability with transient oral mucocal contact, with adhesive layers ensuring compatability with the European food directive legislation, FDA 175.105 and the German recommendations XIV as published by BfR. This construction should also be classed as a safe product in accordance with the material description as given by EC directive 92/59, article 2(b) which will ensure safety for repeated use.

The wrap may be used in its own right, but is particularly advantageous when used in combination with the deformable material of the first aspect of the present invention and/or the heater of a second aspect of the present invention, as the overall effect most closely resembles a real cigarette.

In all aspects of the invention, the reservoir is preferably pressurised and is preferably refillable. The refill is preferably carried out through a refill valve at the end of the cigarette opposite to the outlet.

Figure 2:
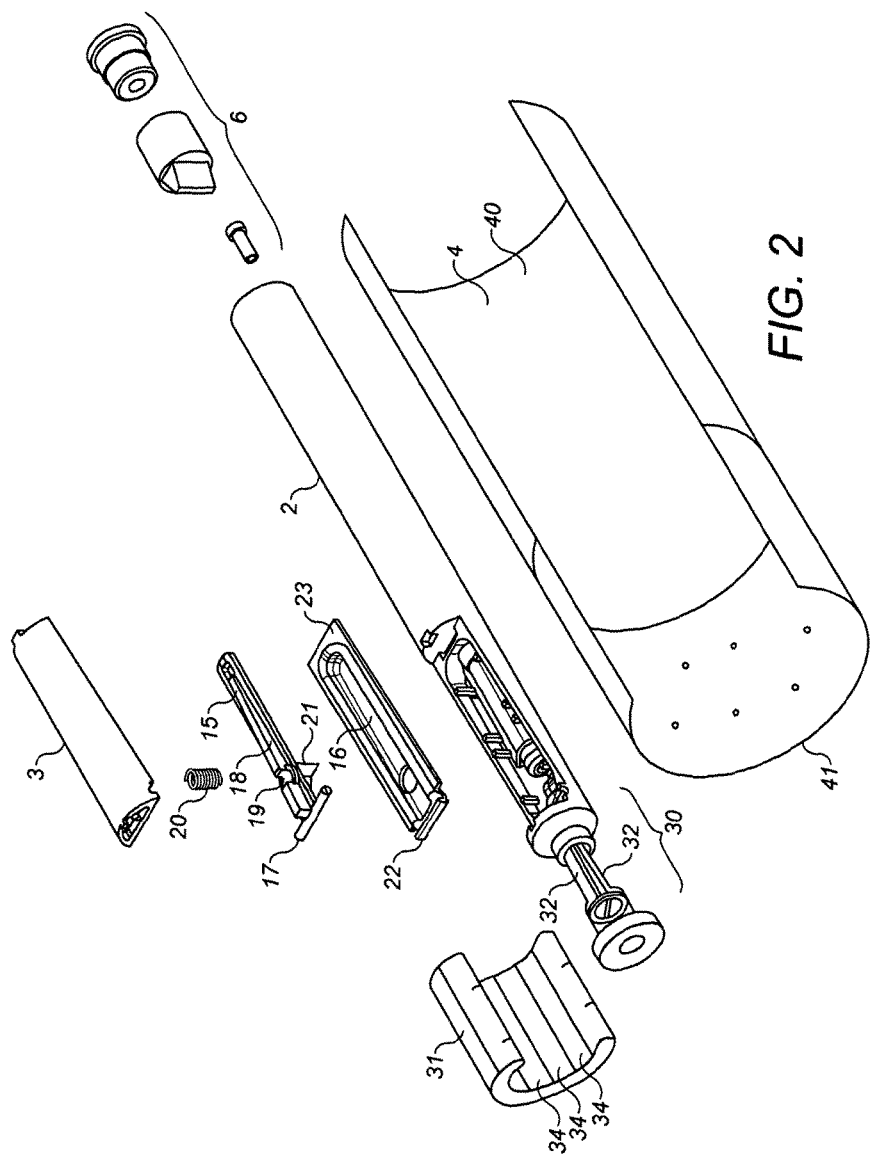
Figure 3A:
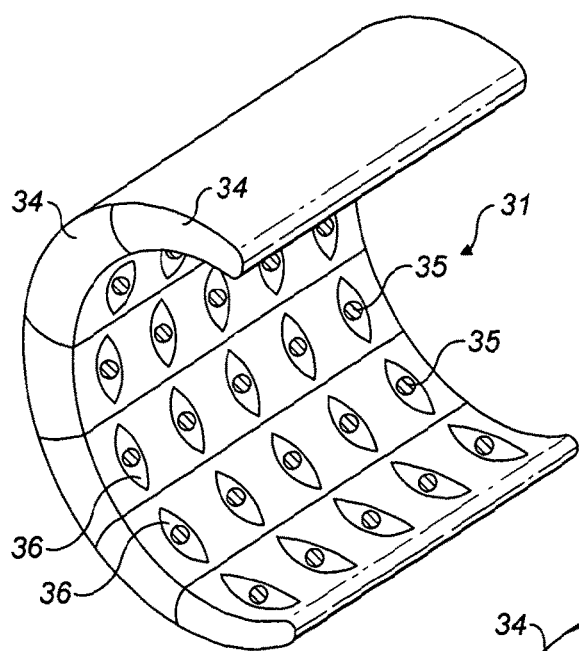
Figure 3B:
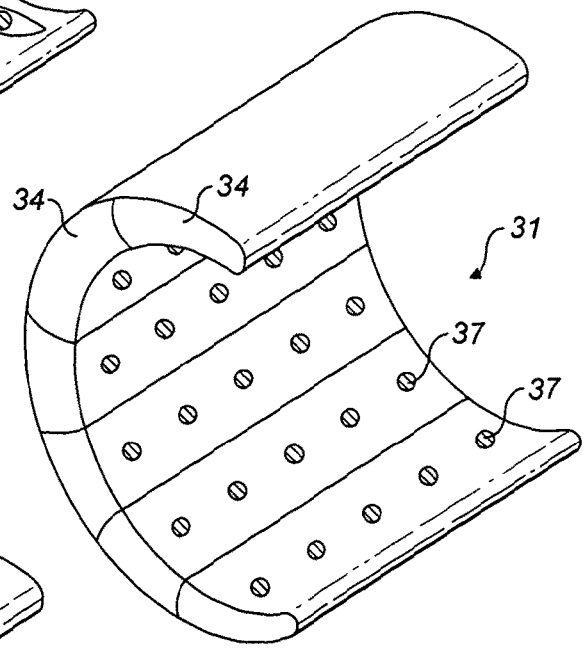
Figure 3C:
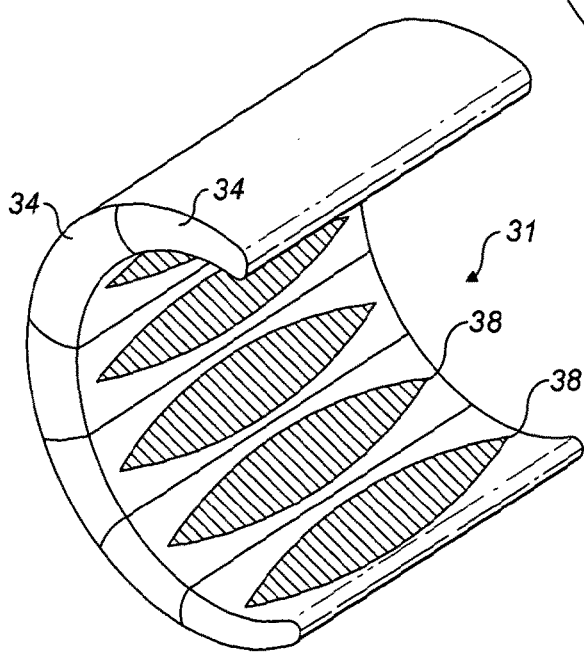
Figure 4:
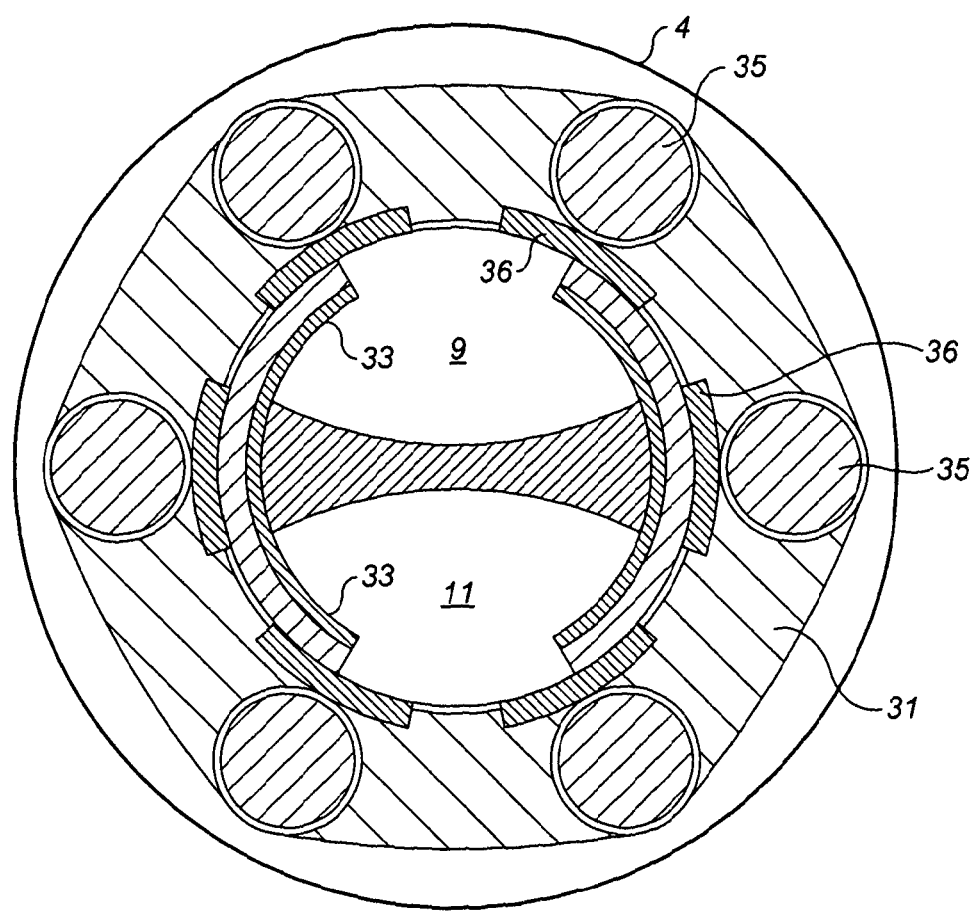

Examples of a simulated cigarette in accordance with the various aspects of the present invention will now be described with reference to the accompany drawings, in which:

FIG. 1 is a cross-section of a simulated cigarette;
FIG. 2 is an exploded view of the simulated cigarette;
FIGS. 3A to 3C are perspective views of alternative deformable members; and
FIG. 4 is a cross-section of the FIG. 3A example.

The device has a housing 1 made up of a main chassis 2 and a closure element 3 as shown in FIG. 2. This is held in place by label 4. Within the housing, there is a reservoir 5 containing the inhalable composition. This is preferably pressurised but could also work with a non-pressurised reservoir in combination with a Venturi nozzle to generate an enhanced suction force on the reservoir. It may be refillable as described in WO 2009/001082 through the filling valve 6, or the device may be a single use device, or may be arranged so that the reservoir 5 is a replaceable component.

The breath-activated valve 7 is positioned between an outlet end 8 and the reservoir 5. The breath-activated valve is arranged so that, when a user sucks on the outlet end 8, the breath-activated valve 7 opens to allow the inhalable composition from the reservoir 5 to be inhaled.

The housing downstream at the valve 7 has two passages. The first of these is the suction passage 9 which communicates with a chamber 10 as will be described in greater detail below and the second is a composition passage 11 from which the inhalable composition is dispensed. This is also described in more detail below. The suction passage and composition passage meet at outlet passage 13 which leads to outlet end 8.

A deformable tubular nozzle 14 is provided between the reservoir 5 and composition passage 11. The element is selectively deformable between open and closed configurations by a mechanism as described below.

This mechanism comprises a pivotally mounted vane 15 and a membrane 16. The pivotally mounted vane has a pivot 17 at the end closest to the outlet end 8 and a central reinforcing rib 18 running along its length and tapering away from the outlet end. At around the midpoint, the vane 15 is provided with a recess 19 for receiving a spring 20 which biases it into the closed position shown in FIG. 1. Below the recess 19 is a jaw 21 having a triangular cross-section which is configured to apply the force provided from the vane 15 to the nozzle 14 over a narrow area (although the nozzle is shown in FIG. 1 in its uncompressed, open state, whereas in use, with the vane in this position it would deform the nozzle to seal the reservoir). The vane 15 is supported by the diaphragm 16 which is sealed to the housing at its ends 22, 23.

An inlet 24 is provided into the chamber 10, while the underside of the membrane 16 is open to atmospheric pressure as a leakage path exists through the housing 1 which is not shown in the drawings as it is not shown in the plane of FIGS. 1 and 2.

When a user sucks on the outlet end 8 air is sucked through inlet 24 through chamber 10 and out of suction passage 9 thereby lowering the pressure in the chamber 10. This causes the vane 15 to be lifted against the action of the spring 20 deforming the diaphragm and lifting the jaw 21 to allow the deformable nozzle 14 to open, thereby allowing the inhalable composition from the reservoir 5 along composition passage 11 into the outlet passage 13 where it mixes with the suction air. The degree of suction applied by the user will determine the extent to which the vane 15 moves and therefore the amount of composition that the user receives. As soon as a user stops sucking, atmospheric pressure will return to the chamber 10 and the spring 20 will push the vane down thereby pinching the nozzle 14 closed.

The simulated cigarette described to date is generally as described in WO 2011/015825.

The housing 1 is provided at the outlet end with a generally annular recess 30 surrounding the outlet passage 13. Within this annular recess is a deformable member 31 which, in situ, is flush with the surface of the housing 1 as shown in FIG. 1. The deformable member 31 may be an elastomeric member, or may be a thin-walled capsule containing a liquid or gel which is described in more detail below. An annular lip 32 is present at the outlet end of the cigarette. This may be thinner than the illustrated lip, or may not be present at all.

The deformable member 31 is generally positioned in the area that would be occupied by the filter of a conventional cigarette. Thus, the user is able to squeeze the end of the cigarette in the manner that they would squeeze the filter of a cigarette, and hold this end of the cigarette in their mouth and, in both cases, obtain a tactile sensation comparable to that of a real cigarette.

Further, the housing 1 in the vicinity of the outlet passage 31 is provided with a pair of diametrically opposed openings 33 and, as shown in FIG. 1, the deformable member 31 is arranged to bulge through these to project into the outlet passage 13. As the user presses on the deformable member, the degree to which the deformable member bulges into the passage 13 is varied. If the user presses on the top of the deformable member 31 (with reference to the orientation shown in FIG. 1), they will restrict the flow through the suction passage 9 with the effect that the user will need to suck harder on the device to achieve the desired inhalation profile. If they press on the lower part of the deformable member 31, they will restrict the flow through the composition passage 11 with the effect that if the valve is fully open, the velocity of the flow will increase and quicken the route of delivery. Pressing on the top and bottom of the deformable member 31 simultaneously will increase the resistance and necessatitate sucking harder on the device but also by nature of construction of the composition passage 11, quicken the flow and speed of delivery. This is a useful feature for smokers who wish to quicken the rate of absorption when undergoing a spike in craving. Thus a user is able to self-regulate the flow of inhalable composition from the cigarette, much as they are able to do with a conventional cigarette by squeezing on the filter.

As well as providing tactile benefits, and the ability to regulate the flow, the deformable member 31 may also be designed as a heater.

As mentioned above, the deformable member 31 may contain liquid or gel. This may be an acetate, and preferably sodium acetate that is super saturated. This may be encapsulated into microcapsules having a polymeric or celluostic casing. If there are around 20 such microcapsules, the device can be re-used a number of times, each time breaking a small number of the capsules. Inside the deformable member 31 and surrounding the inner wall is a layer, disc or film of ferrous metal or other that have been coursed to provide a greater reactive surface area. When the user taps the outer wall of the deformable element 31, such as a smoker is accustomed to do to release ash that has built-up on the tip of the cigarette, crystals of sodium acetate are released into the solution which then act as nucleation sites. This causes the solution to crystallise suddenly, releasing energy and thereby creating a heating effect to the surrounding material, which the user can perceive. This heat can be controlled to ensure that the temperature is pleasant and warming and does not approach higher temperatures that may impact on the integrity of the device. In order to last over several refills of the device, the deformable member 31 may be composed of multiple layers or compartments 34, each connected individually to separate solutions and ferrous metals. It is possible that the outer wall of the deformable member 31 may be a good insulator which allows minimal heat to be conducted out of the device so that the heat is, instead, directed inwardly to heat the flow through the upper passage 13.

Alternative designs of deformable element 31 are shown in FIGS. 3A-3C and 4. In FIGS. 3A and 4, a plurality of frangible balls 35 containing acetate are each positioned on a ferrous disc 36 which provides the nucleation sites. Pressure on the outer wall of the deformable member breaks some of the frangible balls so that the acetate comes into contact with the ferrous disc initiating nucleation and causing an exothermic reaction.

In FIG. 3B, the compartments 34 are filled with calcium powder and frangible balls 37 containing water are arranged along the length of each compartment. Again, pressure on the deformable member 31 breaks the balls 37 and the water and calcium chloride react exothermically.

In FIG. 3C, each compartment 34 contains an elongate ferrous disc 38, the compartment filled with acetate. In this case, pressure on the deformable member 31 causes a sudden "snap" deformation of a disc 38 to trigger nucleation.

Other chemical heating sources for example can include, but not limited to, utilising an in situ combination of calcium chloride and reservoir containing pure distilled water. The calcium chloride is separated from water by a the film or a diaphragm which when tapped or pushed, loses the integrity of its casing and allows the water to dissipate and therefore causing an exothermic reaction to take place. For use in a multi-phase manner, the distilled water can be manufactured into microcapsules, pellets or spheres encompassed either a polymeric or cellulosic casing that are no more than 2 mm in diameter. These microcapsules can be located within the chamber and distributed evenly around a surrounding layer of finely milled calcium chloride powder. When a user squeezes the deformable member 31, element of the mouthpiece, pressure is applied to the microcapsules such that they casing ruptures and releases its containment of the distilled water. There can be arranged around 20 microspheres within the deformable chamber such that there scope for multi-activation during the use of the cigarette device.

As can be seen in FIG. 1, the jaw 21 which represents the effective outlet from the reservoir 5 is positioned some considerable distance from the outlet end 8. This distance is preferably greater than 10 mm. This means that the composition has to flow a reasonable distance through the device before it is inhaled by the smoker. Thus, it can be warmed by the housing surrounding the composition passage 11 and outlet passage 13. It is diluted and warmed by the air from the suction passage 9 and is also heated by the heat generated in the deformable member 31 if this is designed as the exothermic element described above. The smoker therefore inhales composition which is warmed to a degree ideally replicating the temperature of smoke from a real cigarette, but at least warmed to a degree so as not to cause discomfort.

The label 4 is an overwrap that surrounds substantially the entire curved surface of the simulated cigarette. As shown in FIG. 2, it is divided into two sections 40 and 41 which are coloured and patterned to resemble a conventional cigarette with a filter tip. In combination with the deformable member 31, the outlet end of the cigarette both looks and feels like the filter of a conventional cigarette. The label has at least one hole laser drilled so as not to obstruct inlet 24.

The coatings applied to the label 4 demonstrate hydrophobic properties, but also create a lipophobic and oleophobic surface to repel water, dirt on surfaces and any formulation that may be spilled or accidentally emitted during the refilling process. This makes sure that the cigarette paper does not tear or blemish as the formulation may contain propylene glycol, PEG or aromatic oils which will lead to quick discolouration of the paper, and reduce its structural integrity. As such coatings can be used such as a phosphonate based application, and applied in a monolayer. This can be provided by for example Aculon Inc. This will also impart an additional wipe clean quality, so that the dirt does not build up on the mouthpiece. Since the device is intended to be disposable, a coating can be applied solely to the mouthpiece and to the distal end where the refill valve is, to reduce the likelihood of dirt ingress and paper tear. This also provides an enhanced consumer response so that users can clean the mouthpiece end easily without fear or paper or fabric tear, for example if lipstick is accidentally applied.

Additionally fluropolymers can be used, either applied directly to the paper or fabric coating as a powder or spray and provide necessary oil-repellant/water-repellant properties. These can include PTFE (polytetrafluoroethylene), PFA (perfluoroalkoxy polymer resin), FEP (fluorinated ethylene-propylene) and ETFE polyethylenetetrafluoroethylene but not limited to these types of fluoropolymers. Care is taken when choosing a coating that they demonstrate suitable biomaterial compatibility especially if in frequent contact with the skin.

The wrap may be paper-like material such as a tightly woven cotton, or other fabric and a coating of silica or titania particles can be used to provide hydrophobic properties on devices where the oleophobic property is not needed due to a different composition of formulation.

Preferably a material is used that contains a hydrophobic, lipophobic and oleophobic property but also has a fire retardant capability. This is to protect the device in case it unduly exposed to fire or naked flame. Such coatings can include Aluminium Trihydride (ATH), Antimony Trioxide (Sb2O3) and Zinc Borate. Zinc Oxides can also be used at a pharmaceutical grade specifications for use in this respect.

A specialty chemical, MP Protect, available at TSC Ltd, can also be applied which incorporates a fire retardant system for cellulose rich substrates, such as wood, paper cotton and certain textile applications. This will allow it to be capable of withstanding flames in accordance with the DIN 53438 standard burn test, but also has a property to impart an anti-bacterial quality which can destroy microorganisms such as influenza, salmonella and Legionella. This can be an important attribute to the device if shared routinely in social situations.

An anti-bacterial coating on the mouthpiece may be especially advantageous as part of one coating or in addition to several coatings but locally applied on the mouthpiece. Such coatings can include a thin layer of silver, Ionizable silver incorporated into fabric, silver alloy or oxide which will help in reducing the bacteria spread and have been approved for use in respiratory devices such as endotracheal breathing tubes by the FDA. This will offer an improved hygienic aspect to the device if used multiple times before it is eventually disposed of.

The invention claimed is:

1. A simulated cigarette comprising a housing having a generally cigarette-like shape and size; a reservoir of inhalable composition within the housing; an actuator controlling the flow of the inhalable composition from the reservoir; and an outlet passage from the actuator to an outlet in the housing from which outlet a user inhales the composition, wherein the housing is wrapped in a wrap comprising, in order a number of layers comprising a laminate, beginning at the side closest to the housing the layers comprise, in order, an adhesive layer to stick to the housing a paper layer, an ink and a polymer film to cover and protect the paper layer; and the polymer film is lipohobic, oleophobic or lipohobic and oleophobic.

2. A simulated cigarette according to claim 1, wherein the polymer is hydrophobic.

3. A simulated cigarette according to claim 1, wherein the wrap has at least one hole aligned with a flow path in the housing.

4. A simulated cigarette according to claim 1, wherein the wrap adjacent to the outlet is provided with an antibacterial agent.

* * * * *